United States Patent
Smith et al.

(10) Patent No.: US 7,732,167 B2
(45) Date of Patent: Jun. 8, 2010

(54) INTERFERON-α/β BINDING FUSION PROTEINS AND THERAPEUTIC USES THEREOF

(75) Inventors: Eric Smith, New York, NY (US); Margaret Karow, Putnam Valley, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 211 days.

(21) Appl. No.: 11/453,530

(22) Filed: Jun. 15, 2006

(65) Prior Publication Data

US 2006/0286641 A1    Dec. 21, 2006

Related U.S. Application Data

(60) Provisional application No. 60/691,551, filed on Jun. 17, 2005.

(51) Int. Cl.
| | |
|---|---|
| C12P 21/04 | (2006.01) |
| C12N 15/00 | (2006.01) |
| C12N 5/00 | (2006.01) |
| C07K 14/435 | (2006.01) |
| C07H 21/04 | (2006.01) |

(52) U.S. Cl. .......... 435/69.7; 530/350; 435/320.1; 435/325; 536/23.4

(58) Field of Classification Search ............ None
See application file for complete search history.

(56) References Cited

U.S. PATENT DOCUMENTS

| | | | | |
|---|---|---|---|---|
| 6,472,179 | B2 * | 10/2002 | Stahl et al. | 435/69.7 |
| 6,475,983 | B1 * | 11/2002 | Eid et al. | 514/2 |
| 6,713,609 | B1 * | 3/2004 | Chuntharapai et al. | 530/388.22 |
| 7,083,950 | B2 * | 8/2006 | Stahl et al. | 435/69.7 |
| 2003/0018174 | A1 * | 1/2003 | Kim et al. | 530/388.23 |

* cited by examiner

*Primary Examiner*—Marianne P Allen
(74) *Attorney, Agent, or Firm*—Valeta Gregg, Esq.; Izumi Yokoyama, Esq.

(57) ABSTRACT

Polypeptides and multimeric polypeptides capable of binding interferon α and/or interferon β which are useful therapeutically in methods of treating interferon α/β-related conditions or diseases.

20 Claims, No Drawings

SEQUENCE LISTING

<160> NUMBER OF SEQ ID NOS: 9

<210> SEQ ID NO 1
<211> LENGTH: 1308
<212> TYPE: DNA
<213> ORGANISM: Homo sapiens

<400> SEQUENCE: 1

```
atgatggtcg tcctcctggg cgcgacgacc ctagtgctcg tcgccgtggg cccatggggtg      60 ttgtccgcag ccgcaggtgg aaaaaatcta aatctcctc aaaaagtaga ggtcgacatc      120
atagatgaca actttatcct gaggtggaac aggagcgatg agtctgtcgg gaatgtgact      180 tttcattcg attatcaaaa aactgggatg gataattgga taaaattgtc tgggtgtcag      240
aatattacta gtaccaaatg caacttttct tcactcaagc tgaatgttta tgaagaaatt      300
aaattgcgta taagagcaga aaaagaaaac acttcttcat ggtatgaggt tgactcattt      360 acaccattc gcaaagctca gattggtcct ccagaagtac atttagaagc tgaagataag      420
gcaatagtga tacacatctc tcctggaaca aaagatagtg ttatgtggc tttggatggt      480 ttaagcttta catatagctt acttatctgg aaaaactctc caggtgtaga agaaaggatt      540
gaaaatattt attccagaca taaaatttat aaactctcac cagagactac ttattgtcta      600
aaagttaaag cagcactact tacgtcatgg aaaattggtg tctatagtcc agtacattgt      660
ataaagacca cagttgaaaa tgaactacct ccaccagaaa atatagaagt cagtgtccaa      720
aatcagaact atgttcttaa atgggattat acatatgcaa acatgacctt tcaagttcag      780
tggctccacg ccttttttaaa aaggaatcct ggaaaccatt tgtataaatg gaaacaaata      840
cctgactgtg aaaatgtcaa aactacccag tgtgtctttc ctcaaaacgt tttccaaaaa      900
```

```
ggaatttacc ttctccgcgt acaagcatct gatggaaata acacatcttt ttggtctgaa    960
gagataaagt ttgatactga aatacaagct ttcctacttc ctccagtctt taacattaga   1020
tcccttagtg attcattcca tatctatatc ggtgctccaa acagtctgg aaacacgcct    1080 gtgatccagg attatccact gatttatgaa attattttt gggaaaacac ttcaaatgct    1140
gagagaaaaa ttatcgagaa aaaaactgat gttacagttc ctaatttgaa accactgact   1200
gtatattgtg tgaaagccag agcacacacc atggatgaaa agctgaataa agcagtgtt    1260 tttagtgacg ctgtatgtga gaaaacaaaa ccaggaaata cctctaaa               1308
```

```
<210> SEQ ID NO 2
<211> LENGTH: 436
<212> TYPE: PRT
<213> ORGANISM: Homo sapiens

<400> SEQUENCE: 2
```

| | | | | | | | | | | | | | | | |
|---|---|---|---|---|---|---|---|---|---|---|---|---|---|---|---|
| Met | Met | Val | Val | Leu | Leu | Gly | Ala | Thr | Thr | Leu | Val | Leu | Val | Ala | Val |
| 1 | | | | 5 | | | | | 10 | | | | | 15 | |
| Gly | Pro | Trp | Val | Leu | Ser | Ala | Ala | Gly | Gly | Lys | Asn | Leu | Lys | Ser | |
| | | | 20 | | | | | 25 | | | | | 30 | | |
| Pro | Gln | Lys | Val | Glu | Val | Asp | Ile | Ile | Asp | Asp | Asn | Phe | Ile | Leu | Arg |
| | | 35 | | | | | 40 | | | | | 45 | | | |
| Trp | Asn | Arg | Ser | Asp | Glu | Ser | Val | Gly | Asn | Val | Thr | Phe | Ser | Phe | Asp |
| | 50 | | | | | 55 | | | | | 60 | | | | |
| Tyr | Gln | Lys | Thr | Gly | Met | Asp | Asn | Trp | Ile | Lys | Leu | Ser | Gly | Cys | Gln |
| 65 | | | | | 70 | | | | | 75 | | | | | 80 |
| Asn | Ile | Thr | Ser | Thr | Lys | Cys | Asn | Phe | Ser | Ser | Leu | Lys | Leu | Asn | Val |
| | | | | 85 | | | | | 90 | | | | | 95 | |
| Tyr | Glu | Glu | Ile | Lys | Leu | Arg | Ile | Arg | Ala | Glu | Lys | Glu | Asn | Thr | Ser |
| | | | 100 | | | | | 105 | | | | | 110 | | |
| Ser | Trp | Tyr | Glu | Val | Asp | Ser | Phe | Thr | Pro | Phe | Arg | Lys | Ala | Gln | Ile |
| | | 115 | | | | | 120 | | | | | 125 | | | |
| Gly | Pro | Pro | Glu | Val | His | Leu | Glu | Ala | Glu | Asp | Lys | Ala | Ile | Val | Ile |
| | 130 | | | | | 135 | | | | | 140 | | | | |
| His | Ile | Ser | Pro | Gly | Thr | Lys | Asp | Ser | Val | Met | Trp | Ala | Leu | Asp | Gly |
| 145 | | | | | 150 | | | | | 155 | | | | | 160 |
| Leu | Ser | Phe | Thr | Tyr | Ser | Leu | Leu | Ile | Trp | Lys | Asn | Ser | Ser | Gly | Val |
| | | | | 165 | | | | | 170 | | | | | 175 | |
| Glu | Glu | Arg | Ile | Glu | Asn | Ile | Tyr | Ser | Arg | His | Lys | Ile | Tyr | Lys | Leu |
| | | | 180 | | | | | 185 | | | | | 190 | | |
| Ser | Pro | Glu | Thr | Thr | Tyr | Cys | Leu | Lys | Val | Lys | Ala | Ala | Leu | Leu | Thr |
| | | 195 | | | | | 200 | | | | | 205 | | | |
| Ser | Trp | Lys | Ile | Gly | Val | Tyr | Ser | Pro | Val | His | Cys | Ile | Lys | Thr | Thr |
| | 210 | | | | | 215 | | | | | 220 | | | | |
| Val | Glu | Asn | Glu | Leu | Pro | Pro | Glu | Asn | Ile | Glu | Val | Ser | Val | Gln |
| 225 | | | | | 230 | | | | | 235 | | | | | 240 |
| Asn | Gln | Asn | Tyr | Val | Leu | Lys | Trp | Asp | Tyr | Thr | Tyr | Ala | Asn | Met | Thr |
| | | | | 245 | | | | | 250 | | | | | 255 | |
| Phe | Gln | Val | Gln | Trp | Leu | His | Ala | Phe | Leu | Lys | Arg | Asn | Pro | Gly | Asn |
| | | | 260 | | | | | 265 | | | | | 270 | | |
| His | Leu | Tyr | Lys | Trp | Lys | Gln | Ile | Pro | Asp | Cys | Glu | Asn | Val | Lys | Thr |
| | | 275 | | | | | 280 | | | | | 285 | | | |
| Thr | Gln | Cys | Val | Phe | Pro | Gln | Asn | Val | Phe | Gln | Lys | Gly | Ile | Tyr | Leu |
| | 290 | | | | | 295 | | | | | 300 | | | | |

```
Leu Arg Val Gln Ala Ser Asp Gly Asn Asn Thr Ser Phe Trp Ser Glu
305                 310                 315                 320

Glu Ile Lys Phe Asp Thr Glu Ile Gln Ala Phe Leu Leu Pro Pro Val
            325                 330                 335

Phe Asn Ile Arg Ser Leu Ser Asp Ser Phe His Ile Tyr Ile Gly Ala
        340                 345                 350

Pro Lys Gln Ser Gly Asn Thr Pro Val Ile Gln Asp Tyr Pro Leu Ile
    355                 360                 365

Tyr Glu Ile Ile Phe Trp Glu Asn Thr Ser Asn Ala Glu Arg Lys Ile
370                 375                 380

Ile Glu Lys Lys Thr Asp Val Thr Val Pro Asn Leu Lys Pro Leu Thr
385                 390                 395                 400

Val Tyr Cys Val Lys Ala Arg Ala His Thr Met Asp Glu Lys Leu Asn
                405                 410                 415

Lys Ser Ser Val Phe Ser Asp Ala Val Cys Glu Lys Thr Lys Pro Gly
            420                 425                 430

Asn Thr Ser Lys
        435

<210> SEQ ID NO 3
<211> LENGTH: 729
<212> TYPE: DNA
<213> ORGANISM: Homo sapiens

<400> SEQUENCE: 3
atgcttttga gccagaatgc cttcatcttc agatcactta atttggttct catggtgtat       60
atcagcctcg tgtttggtat ttcatatgat tcgcctgatt acacagatga atcttgcact      120
ttcaagatat cattgcgaaa tttccggtcc atcttatcat gggaattaaa aaaccactcc      180
attgtaccaa ctcactatac attgctgtat acaatcatga gtaaaccaga agatttgaag      240
gtggttaaga actgtgcaaa taccacaaga tcattttgtg acctcacaga tgagtggaga      300
agcacacacg aggcctatgt caccgtccta gaaggattca gcgggaacac aacgttgttc      360
agttgctcac acaatttctg ctggccata gacatgtctt ttgaaccacc agagtttgag       420
attgttggtt ttaccaacca cattaatgtg atggtgaaat ttccatctat tgttgaggaa      480
gaattacagt ttgatttatc tctcgtcatt gaagaacagt cagagggaat tgttaagaag      540
cataaacccg aaataaaagg aaacatgagt ggaaatttca cctatatcat tgacaagtta      600
attccaaaca cgaactactg tgtatctgtt tatttagagc acagtgatga gcaagcagta      660
ataaagtctc ccttaaaatg caccctcctt ccacctggcc aggaatcaga atcagcagaa      720
tctgccaaa                                                              729

<210> SEQ ID NO 4
<211> LENGTH: 243
<212> TYPE: PRT
<213> ORGANISM: Homo sapiens

<400> SEQUENCE: 4

Met Leu Leu Ser Gln Asn Ala Phe Ile Phe Arg Ser Leu Asn Leu Val
1               5                   10                  15

Leu Met Val Tyr Ile Ser Leu Val Phe Gly Ile Ser Tyr Asp Ser Pro
            20                  25                  30

Asp Tyr Thr Asp Glu Ser Cys Thr Phe Lys Ile Ser Leu Arg Asn Phe
        35                  40                  45
```

```
Arg Ser Ile Leu Ser Trp Glu Leu Lys Asn His Ser Ile Val Pro Thr
 50                  55                  60

His Tyr Thr Leu Leu Tyr Thr Ile Met Ser Lys Pro Glu Asp Leu Lys
 65                  70                  75                  80

Val Val Lys Asn Cys Ala Asn Thr Thr Arg Ser Phe Cys Asp Leu Thr
                 85                  90                  95

Asp Glu Trp Arg Ser Thr His Glu Ala Tyr Val Thr Val Leu Glu Gly
            100                 105                 110

Phe Ser Gly Asn Thr Thr Leu Phe Ser Cys Ser His Asn Phe Trp Leu
            115                 120                 125

Ala Ile Asp Met Ser Phe Glu Pro Pro Glu Phe Glu Ile Val Gly Phe
130                 135                 140

Thr Asn His Ile Asn Val Met Val Lys Phe Pro Ser Ile Val Glu Glu
145                 150                 155                 160

Glu Leu Gln Phe Asp Leu Ser Leu Val Ile Glu Gln Ser Glu Gly
                165                 170                 175

Ile Val Lys Lys His Lys Pro Glu Ile Lys Gly Asn Met Ser Gly Asn
            180                 185                 190

Phe Thr Tyr Ile Ile Asp Lys Leu Ile Pro Asn Thr Asn Tyr Cys Val
            195                 200                 205

Ser Val Tyr Leu Glu His Ser Asp Glu Gln Ala Val Ile Lys Ser Pro
210                 215                 220

Leu Lys Cys Thr Leu Leu Pro Pro Gly Gln Glu Ser Glu Ser Ala Glu
225                 230                 235                 240

Ser Ala Lys

<210> SEQ ID NO 5
<211> LENGTH: 29
<212> TYPE: PRT
<213> ORGANISM: Artificial Sequence
<220> FEATURE:
<223> OTHER INFORMATION: Synthetic

<400> SEQUENCE: 5

Met His Arg Pro Arg Arg Arg Gly Thr Arg Pro Pro Leu Ala Leu
 1               5                  10                  15

Leu Ala Leu Leu Leu Ala Ala Arg Gly Ala Asp Ala
            20                  25

<210> SEQ ID NO 6
<211> LENGTH: 859
<212> TYPE: PRT
<213> ORGANISM: Artificial Sequence
<220> FEATURE:
<223> OTHER INFORMATION: Synthetic

<400> SEQUENCE: 6

Arg Ser Ile Ser Tyr Asp Ser Pro Asp Tyr Thr Asp Glu Ser Cys Thr
 1               5                  10                  15

Phe Lys Ile Ser Leu Arg Asn Phe Arg Ser Ile Leu Ser Trp Glu Leu
             20                  25                  30

Lys Asn His Ser Ile Val Pro Thr His Tyr Thr Leu Leu Tyr Thr Ile
             35                  40                  45

Met Ser Lys Pro Glu Asp Leu Lys Val Val Lys Asn Cys Ala Asn Thr
 50                  55                  60

Thr Arg Ser Phe Cys Asp Leu Thr Asp Glu Trp Arg Ser Thr His Glu
 65                  70                  75                  80
```

-continued

```
Ala Tyr Val Thr Val Leu Glu Gly Phe Ser Gly Asn Thr Thr Leu Phe
             85                  90                  95

Ser Cys Ser His Asn Phe Trp Leu Ala Ile Asp Met Ser Phe Glu Pro
            100                 105                 110

Pro Glu Phe Glu Ile Val Gly Phe Thr Asn His Ile Asn Val Met Val
        115                 120                 125

Lys Phe Pro Ser Ile Val Glu Glu Leu Gln Phe Asp Leu Ser Leu
130                 135                 140

Val Ile Glu Glu Gln Ser Glu Gly Ile Val Lys Lys His Lys Pro Glu
145                 150                 155                 160

Ile Lys Gly Asn Met Ser Gly Asn Phe Thr Tyr Ile Ile Asp Lys Leu
                165                 170                 175

Ile Pro Asn Thr Asn Tyr Cys Val Ser Val Tyr Leu Glu His Ser Asp
            180                 185                 190

Glu Gln Ala Val Ile Lys Ser Pro Leu Lys Cys Thr Leu Leu Pro Pro
        195                 200                 205

Gly Gln Glu Ser Glu Ser Ala Glu Ser Ala Lys Arg Ser Lys Asn Leu
    210                 215                 220

Lys Ser Pro Gln Lys Val Glu Val Asp Ile Ile Asp Asp Asn Phe Ile
225                 230                 235                 240

Leu Arg Trp Asn Arg Ser Asp Glu Ser Val Gly Asn Val Thr Phe Ser
                245                 250                 255

Phe Asp Tyr Gln Lys Thr Gly Met Asp Asn Trp Ile Lys Leu Ser Gly
            260                 265                 270

Cys Gln Asn Ile Thr Ser Thr Lys Cys Asn Phe Ser Ser Leu Lys Leu
        275                 280                 285

Asn Val Tyr Glu Glu Ile Lys Leu Arg Ile Arg Ala Glu Lys Glu Asn
    290                 295                 300

Thr Ser Ser Trp Tyr Glu Val Asp Ser Phe Thr Pro Phe Arg Lys Ala
305                 310                 315                 320

Gln Ile Gly Pro Pro Glu Val His Leu Glu Ala Glu Asp Lys Ala Ile
                325                 330                 335

Val Ile His Ile Ser Pro Gly Thr Lys Asp Ser Val Met Trp Ala Leu
            340                 345                 350

Asp Gly Leu Ser Phe Thr Tyr Ser Leu Val Ile Trp Lys Asn Ser Ser
        355                 360                 365

Gly Val Glu Glu Arg Ile Glu Asn Ile Tyr Ser Arg His Lys Ile Tyr
    370                 375                 380

Lys Leu Ser Pro Glu Thr Thr Tyr Cys Leu Lys Val Lys Ala Ala Leu
385                 390                 395                 400

Leu Thr Ser Trp Lys Ile Gly Val Tyr Ser Pro Val His Cys Ile Lys
                405                 410                 415

Thr Thr Val Glu Asn Glu Leu Pro Pro Pro Glu Asn Ile Glu Val Ser
            420                 425                 430

Val Gln Asn Gln Asn Tyr Val Leu Lys Trp Asp Tyr Thr Tyr Ala Asn
        435                 440                 445

Met Thr Phe Gln Val Gln Trp Leu His Ala Phe Leu Lys Arg Asn Pro
    450                 455                 460

Gly Asn His Leu Tyr Lys Trp Lys Gln Ile Pro Asp Cys Glu Asn Val
465                 470                 475                 480

Lys Thr Thr Gln Cys Val Phe Pro Gln Asn Val Phe Gln Lys Gly Ile
                485                 490                 495

Tyr Leu Leu Arg Val Gln Ala Ser Asp Gly Asn Asn Thr Ser Phe Trp
```

```
                        500                 505                 510
Ser Glu Glu Ile Lys Phe Asp Thr Glu Ile Gln Ala Phe Leu Leu Pro
        515                 520                 525

Pro Val Phe Asn Ile Arg Ser Leu Ser Asp Ser Phe His Ile Tyr Ile
        530                 535                 540

Gly Ala Pro Lys Gln Ser Gly Asn Thr Pro Val Ile Gln Asp Tyr Pro
545                 550                 555                 560

Leu Ile Tyr Glu Ile Phe Trp Glu Asn Thr Ser Asn Ala Glu Arg
                565                 570                 575

Lys Ile Ile Glu Lys Thr Asp Val Thr Val Pro Asn Leu Lys Pro
            580                 585                 590

Leu Thr Val Tyr Cys Val Lys Ala Arg Ala His Thr Met Asp Glu Lys
            595                 600                 605

Leu Asn Lys Ser Ser Val Phe Ser Asp Ala Val Cys Glu Lys Thr Lys
            610                 615                 620

Pro Gly Asn Thr Ser Lys Ser Gly Asp Lys Thr His Thr Cys Pro Pro
625                 630                 635                 640

Cys Pro Ala Pro Glu Leu Leu Gly Gly Pro Ser Val Phe Leu Phe Pro
                645                 650                 655

Pro Lys Pro Lys Asp Thr Leu Met Ile Ser Arg Thr Pro Glu Val Thr
            660                 665                 670

Cys Val Val Val Asp Val Ser His Glu Asp Pro Glu Val Lys Phe Asn
            675                 680                 685

Trp Tyr Val Asp Gly Val Glu Val His Asn Ala Lys Thr Lys Pro Arg
            690                 695                 700

Glu Glu Gln Tyr Asn Ser Thr Tyr Arg Val Val Ser Val Leu Thr Val
705                 710                 715                 720

Leu His Gln Asp Trp Leu Asn Gly Lys Glu Tyr Lys Cys Lys Val Ser
                725                 730                 735

Asn Lys Ala Leu Pro Ala Pro Ile Glu Lys Thr Ile Ser Lys Ala Lys
                740                 745                 750

Gly Gln Pro Arg Glu Pro Gln Val Tyr Thr Leu Pro Pro Ser Arg Asp
            755                 760                 765

Glu Leu Thr Lys Asn Gln Val Ser Leu Thr Cys Leu Val Lys Gly Phe
            770                 775                 780

Tyr Pro Ser Asp Ile Ala Val Glu Trp Glu Ser Asn Gly Gln Pro Glu
785                 790                 795                 800

Asn Asn Tyr Lys Thr Thr Pro Pro Val Leu Asp Ser Asp Gly Ser Phe
                805                 810                 815

Phe Leu Tyr Ser Lys Leu Thr Val Asp Lys Ser Arg Trp Gln Gln Gly
                820                 825                 830

Asn Val Phe Ser Cys Ser Val Met His Glu Ala Leu His Asn His Tyr
            835                 840                 845

Thr Gln Lys Ser Leu Ser Leu Ser Pro Gly Lys
        850                 855

<210> SEQ ID NO 7
<211> LENGTH: 640
<212> TYPE: PRT
<213> ORGANISM: Artificial Sequence
<220> FEATURE:
<223> OTHER INFORMATION: Synthetic

<400> SEQUENCE: 7

Arg Ser Lys Asn Leu Lys Ser Pro Gln Lys Val Glu Val Asp Ile Ile
```

```
            1               5                   10                  15
Asp Asp Asn Phe Ile Leu Arg Trp Asn Arg Ser Asp Glu Ser Val Gly
                20                  25                  30

Asn Val Thr Phe Ser Phe Asp Tyr Gln Lys Thr Gly Met Asp Asn Trp
                35                  40                  45

Ile Lys Leu Ser Gly Cys Gln Asn Ile Thr Ser Thr Lys Cys Asn Phe
 50                              55                  60

Ser Ser Leu Lys Leu Asn Val Tyr Glu Glu Ile Lys Leu Arg Ile Arg
 65                  70                  75                  80

Ala Glu Lys Glu Asn Thr Ser Ser Trp Tyr Glu Val Asp Ser Phe Thr
                85                  90                  95

Pro Phe Arg Lys Ala Gln Ile Gly Pro Pro Glu Val His Leu Glu Ala
                100                 105                 110

Glu Asp Lys Ala Ile Val Ile His Ile Ser Pro Gly Thr Lys Asp Ser
                115                 120                 125

Val Met Trp Ala Leu Asp Gly Leu Ser Phe Thr Tyr Ser Leu Val Ile
                130                 135                 140

Trp Lys Asn Ser Ser Gly Val Glu Glu Arg Ile Glu Asn Ile Tyr Ser
145                 150                 155                 160

Arg His Lys Ile Tyr Lys Leu Ser Pro Glu Thr Thr Tyr Cys Leu Lys
                165                 170                 175

Val Lys Ala Ala Leu Leu Thr Ser Trp Lys Ile Gly Val Tyr Ser Pro
                180                 185                 190

Val His Cys Ile Lys Thr Thr Val Glu Asn Glu Leu Pro Pro Pro Glu
                195                 200                 205

Asn Ile Glu Val Ser Val Gln Asn Gln Asn Tyr Val Leu Lys Trp Asp
                210                 215                 220

Tyr Thr Tyr Ala Asn Met Thr Phe Gln Val Gln Trp Leu His Ala Phe
225                 230                 235                 240

Leu Lys Arg Asn Pro Gly Asn His Leu Tyr Lys Trp Lys Gln Ile Pro
                245                 250                 255

Asp Cys Glu Asn Val Lys Thr Thr Gln Cys Val Phe Pro Gln Asn Val
                260                 265                 270

Phe Gln Lys Gly Ile Tyr Leu Leu Arg Val Gln Ala Ser Asp Gly Asn
                275                 280                 285

Asn Thr Ser Phe Trp Ser Glu Glu Ile Lys Phe Asp Thr Glu Ile Gln
                290                 295                 300

Ala Phe Leu Leu Pro Pro Val Phe Asn Ile Arg Ser Leu Ser Asp Ser
305                 310                 315                 320

Phe His Ile Tyr Ile Gly Ala Pro Lys Gln Ser Gly Asn Thr Pro Val
                325                 330                 335

Ile Gln Asp Tyr Pro Leu Ile Tyr Glu Ile Ile Phe Trp Glu Asn Thr
                340                 345                 350

Ser Asn Ala Glu Arg Lys Ile Ile Glu Lys Lys Thr Asp Val Thr Val
                355                 360                 365

Pro Asn Leu Lys Pro Leu Thr Val Tyr Cys Val Lys Ala Arg Ala His
                370                 375                 380

Thr Met Asp Glu Lys Leu Asn Lys Ser Ser Val Phe Ser Asp Ala Val
385                 390                 395                 400

Cys Glu Lys Thr Lys Pro Gly Asn Thr Ser Lys Ser Gly Asp Lys Thr
                405                 410                 415

His Thr Cys Pro Pro Cys Pro Ala Pro Glu Leu Leu Gly Gly Pro Ser
                420                 425                 430
```

```
Val Phe Leu Phe Pro Lys Pro Lys Asp Thr Leu Met Ile Ser Arg
            435                 440                 445

Thr Pro Glu Val Thr Cys Val Val Asp Val Ser His Glu Asp Pro
    450                 455                 460

Glu Val Lys Phe Asn Trp Tyr Val Asp Gly Val Glu Val His Asn Ala
465                 470                 475                 480

Lys Thr Lys Pro Arg Glu Glu Gln Tyr Asn Ser Thr Tyr Arg Val Val
                485                 490                 495

Ser Val Leu Thr Val Leu His Gln Asp Trp Leu Asn Gly Lys Glu Tyr
            500                 505                 510

Lys Cys Lys Val Ser Asn Lys Ala Leu Pro Ala Pro Ile Glu Lys Thr
        515                 520                 525

Ile Ser Lys Ala Lys Gly Gln Pro Arg Glu Pro Gln Val Tyr Thr Leu
    530                 535                 540

Pro Pro Ser Arg Asp Glu Leu Thr Lys Asn Gln Val Ser Leu Thr Cys
545                 550                 555                 560

Leu Val Lys Gly Phe Tyr Pro Ser Asp Ile Ala Val Glu Trp Glu Ser
                565                 570                 575

Asn Gly Gln Pro Glu Asn Asn Tyr Lys Thr Thr Pro Pro Val Leu Asp
            580                 585                 590

Ser Asp Gly Ser Phe Phe Leu Tyr Ser Lys Leu Thr Val Asp Lys Ser
        595                 600                 605

Arg Trp Gln Gln Gly Asn Val Phe Ser Cys Ser Val Met His Glu Ala
610                 615                 620

Leu His Asn His Tyr Thr Gln Lys Ser Leu Ser Leu Ser Pro Gly Lys
625                 630                 635                 640

<210> SEQ ID NO 8
<211> LENGTH: 448
<212> TYPE: PRT
<213> ORGANISM: Artificial Sequence
<220> FEATURE:
<223> OTHER INFORMATION: Synthetic

<400> SEQUENCE: 8

Arg Ser Ile Ser Tyr Asp Ser Pro Asp Tyr Thr Asp Glu Ser Cys Thr
1               5                   10                  15

Phe Lys Ile Ser Leu Arg Asn Phe Arg Ser Ile Leu Ser Trp Glu Leu
            20                  25                  30

Lys Asn His Ser Ile Val Pro Thr His Tyr Thr Leu Leu Tyr Thr Ile
        35                  40                  45

Met Ser Lys Pro Glu Asp Leu Lys Val Val Lys Asn Cys Ala Asn Thr
    50                  55                  60

Thr Arg Ser Phe Cys Asp Leu Thr Asp Glu Trp Arg Ser Thr His Glu
65                  70                  75                  80

Ala Tyr Val Thr Val Leu Glu Gly Phe Ser Gly Asn Thr Thr Leu Phe
                85                  90                  95

Ser Cys Ser His Asn Phe Trp Leu Ala Ile Asp Met Ser Phe Glu Pro
            100                 105                 110

Pro Glu Phe Glu Ile Val Gly Phe Thr Asn His Ile Asn Val Met Val
        115                 120                 125

Lys Phe Pro Ser Ile Val Glu Glu Glu Leu Gln Phe Asp Leu Ser Leu
    130                 135                 140

Val Ile Glu Glu Gln Ser Glu Gly Ile Val Lys Lys His Lys Pro Glu
145                 150                 155                 160
```

Ile Lys Gly Asn Met Ser Gly Asn Phe Thr Tyr Ile Ile Asp Lys Leu
            165                 170                 175

Ile Pro Asn Thr Asn Tyr Cys Val Ser Val Tyr Leu Glu His Ser Asp
            180                 185                 190

Glu Gln Ala Val Ile Lys Ser Pro Leu Lys Cys Thr Leu Leu Pro Pro
            195                 200                 205

Gly Gln Glu Ser Glu Ser Ala Glu Ser Ala Lys Ser Gly Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 9
<211> LENGTH: 740
<212> TYPE: PRT
<213> ORGANISM: Artificial Sequence
<220> FEATURE:
<223> OTHER INFORMATION: Synthetic

<400> SEQUENCE: 9

Arg Ser Thr Asp Glu Ser Cys Thr Phe Lys Ile Ser Leu Arg Asn Phe
1               5                   10                  15

Arg Ser Ile Leu Ser Trp Glu Leu Lys Asn His Ser Ile Val Pro Thr
            20                  25                  30

His Tyr Thr Leu Leu Tyr Thr Ile Met Ser Lys Pro Glu Asp Leu Lys
            35                  40                  45

Val Val Lys Asn Cys Ala Asn Thr Thr Arg Ser Phe Cys Asp Leu Thr
            50                  55                  60

Asp Glu Trp Arg Ser Thr His Glu Ala Tyr Val Thr Val Leu Glu Gly
65              70                  75                  80

-continued

```
Phe Ser Gly Asn Thr Thr Leu Phe Ser Cys Ser His Asn Phe Trp Leu
                85                  90                  95
Ala Ile Asp Met Ser Phe Glu Pro Pro Glu Phe Glu Ile Val Gly Phe
            100                 105                 110
Thr Asn His Ile Asn Val Met Val Lys Phe Pro Ser Ile Val Glu Glu
        115                 120                 125
Glu Leu Gln Phe Asp Leu Ser Leu Val Ile Glu Gln Ser Glu Gly
    130                 135                 140
Ile Val Lys Lys His Lys Pro Glu Ile Lys Gly Asn Met Ser Gly Asn
145                 150                 155                 160
Phe Thr Tyr Ile Ile Asp Lys Leu Ile Pro Asn Thr Asn Tyr Cys Val
                165                 170                 175
Ser Val Tyr Leu Glu His Ser Asp Glu Gln Ala Val Ile Lys Ser Pro
            180                 185                 190
Leu Lys Cys Thr Leu Leu Pro Pro Gly Arg Ser Lys Asn Leu Lys Ser
        195                 200                 205
Pro Gln Lys Val Glu Val Asp Ile Ile Asp Asp Asn Phe Ile Leu Arg
    210                 215                 220
Trp Asn Arg Ser Asp Glu Ser Val Gly Asn Val Thr Phe Ser Phe Asp
225                 230                 235                 240
Tyr Gln Lys Thr Gly Met Asp Asn Trp Ile Lys Leu Ser Gly Cys Gln
                245                 250                 255
Asn Ile Thr Ser Thr Lys Cys Asn Phe Ser Ser Leu Lys Leu Asn Val
            260                 265                 270
Tyr Glu Glu Ile Lys Leu Arg Ile Arg Ala Glu Lys Glu Asn Thr Ser
        275                 280                 285
Ser Trp Tyr Glu Val Asp Ser Phe Thr Pro Phe Arg Lys Ala Gln Ile
    290                 295                 300
Gly Pro Pro Glu Val His Leu Glu Ala Glu Asp Lys Ala Ile Val Ile
305                 310                 315                 320
His Ile Ser Pro Gly Thr Lys Asp Ser Val Met Trp Ala Leu Asp Gly
                325                 330                 335
Leu Ser Phe Thr Tyr Ser Leu Val Ile Trp Lys Asn Ser Ser Gly Val
            340                 345                 350
Glu Glu Arg Ile Glu Asn Ile Tyr Ser Arg His Lys Ile Tyr Lys Leu
        355                 360                 365
Ser Pro Glu Thr Thr Tyr Cys Leu Lys Val Lys Ala Ala Leu Leu Thr
    370                 375                 380
Ser Trp Lys Ile Gly Val Tyr Ser Pro Val His Cys Ile Lys Thr Thr
385                 390                 395                 400
Val Glu Asn Glu Leu Pro Pro Pro Glu Asn Ile Glu Val Ser Val Gln
                405                 410                 415
Asn Gln Asn Tyr Val Leu Lys Trp Asp Tyr Thr Tyr Ala Asn Met Thr
            420                 425                 430
Phe Gln Val Gln Trp Leu His Ala Phe Leu Lys Arg Asn Pro Gly Asn
        435                 440                 445
His Leu Tyr Lys Trp Lys Gln Ile Pro Asp Cys Glu Asn Val Lys Thr
    450                 455                 460
Thr Gln Cys Val Phe Pro Gln Asn Val Phe Gln Lys Gly Ile Tyr Leu
465                 470                 475                 480
Leu Arg Val Gln Ala Ser Asp Gly Asn Asn Thr Ser Phe Trp Ser Glu
                485                 490                 495
```

-continued

| | | | | | | | | | | | | |
|---|---|---|---|---|---|---|---|---|---|---|---|---|
| Glu | Ile | Lys | Phe | Asp | Thr | Glu | Ile | Gln | Ala | Phe | Leu | Leu | Pro | Pro | Ser |
| | | | 500 | | | | 505 | | | | | 510 | | | |
| Gly | Asp | Lys | Thr | His | Thr | Cys | Pro | Pro | Cys | Pro | Ala | Pro | Glu | Leu | Leu |
| | | | 515 | | | | 520 | | | | | 525 | | | |
| Gly | Gly | Pro | Ser | Val | Phe | Leu | Phe | Pro | Pro | Lys | Pro | Lys | Asp | Thr | Leu |
| | | 530 | | | | | 535 | | | | | 540 | | | |
| Met | Ile | Ser | Arg | Thr | Pro | Glu | Val | Thr | Cys | Val | Val | Val | Asp | Val | Ser |
| 545 | | | | | 550 | | | | 555 | | | | | | 560 |
| His | Glu | Asp | Pro | Glu | Val | Lys | Phe | Asn | Trp | Tyr | Val | Asp | Gly | Val | Glu |
| | | | 565 | | | | | 570 | | | | | | 575 | |
| Val | His | Asn | Ala | Lys | Thr | Lys | Pro | Arg | Glu | Glu | Gln | Tyr | Asn | Ser | Thr |
| | | | 580 | | | | | 585 | | | | | 590 | | |
| Tyr | Arg | Val | Val | Ser | Val | Leu | Thr | Val | Leu | His | Gln | Asp | Trp | Leu | Asn |
| | | | 595 | | | | 600 | | | | | 605 | | | |
| Gly | Lys | Glu | Tyr | Lys | Cys | Lys | Val | Ser | Asn | Lys | Ala | Leu | Pro | Ala | Pro |
| | | | 610 | | | | 615 | | | | | 620 | | | |
| Ile | Glu | Lys | Thr | Ile | Ser | Lys | Ala | Lys | Gly | Gln | Pro | Arg | Glu | Pro | Gln |
| 625 | | | | | 630 | | | | | 635 | | | | | 640 |
| Val | Tyr | Thr | Leu | Pro | Pro | Ser | Arg | Asp | Glu | Leu | Thr | Lys | Asn | Gln | Val |
| | | | | 645 | | | | | 650 | | | | | 655 | |
| Ser | Leu | Thr | Cys | Leu | Val | Lys | Gly | Phe | Tyr | Pro | Ser | Asp | Ile | Ala | Val |
| | | | 660 | | | | | 665 | | | | | 670 | | |
| Glu | Trp | Glu | Ser | Asn | Gly | Gln | Pro | Glu | Asn | Asn | Tyr | Lys | Thr | Thr | Pro |
| | | | 675 | | | | | 680 | | | | | 685 | | |
| Pro | Val | Leu | Asp | Ser | Asp | Gly | Ser | Phe | Phe | Leu | Tyr | Ser | Lys | Leu | Thr |
| | | | 690 | | | | 695 | | | | | 700 | | | |
| Val | Asp | Lys | Ser | Arg | Trp | Gln | Gln | Gly | Asn | Val | Phe | Ser | Cys | Ser | Val |
| 705 | | | | | 710 | | | | | 715 | | | | | 720 |
| Met | His | Glu | Ala | Leu | His | Asn | His | Tyr | Thr | Gln | Lys | Ser | Leu | Ser | Leu |
| | | | | 725 | | | | | 730 | | | | | 735 | |
| Ser | Pro | Gly | Lys | | | | | | | | | | | | |
| | | | 740 | | | | | | | | | | | | |

INTERFERON-α/β BINDING FUSION PROTEINS AND THERAPEUTIC USES THEREOF

CROSS-REFERENCE TO RELATED APPLICATIONS

This application claims the benefit under 35 USC §119(e) of U.S. Provisional 60/691,551 filed 17 Jun. 2005, which application is herein specifically incorporated by reference in its entirety.

BACKGROUND OF THE INVENTION

1. Field of the Invention

The invention encompasses interferon α- and/or β-binding fusion proteins, as well as therapeutic uses of such polypeptides for inhibiting interferon α and/or β activity, especially the interferon α proteins.

2. Description of Related Art

It has previously been reported that a humanized anti-interferon α antibody neutralizes human leukocyte interferon and is beneficial in rodent models of insulin-dependent diabetes mellitus (IDDM) (Chuntharapai et al. (2001) Cytokine 15(5):250-260).

BRIEF SUMMARY OF THE INVENTION

In a first aspect, the invention features a nucleic acid molecule encoding an interferon α- and/or interferon β-binding fusion protein $(R1)_x$-$(R2)_y$-F, wherein R1 comprises the extracellular domain of interferon alpha receptor 1 (IFNAR1) component, R2 comprises the extracellular domain of interferon receptor alpha 2 (IFNAR2) component, F is a fusion component, and x and y are each independently a positive integer ≧1, for example between 1 and 10. The extracellular domains of the wild-type human IFNAR1 (SEQ ID NO:2 including signal peptide 1-27) and IFNAR2 (SEQ ID NO:4 including signal peptide 1-26) proteins are encoded by the nucleic acid sequences shown in SEQ ID NO:1 and 3, respectively.

The components of the fusion protein may be arranged in different orders, for example, F-R1-R2, R1-F-R2, R2-F-R1, R2-R1-F, etc. More specifically, R1 is derived from an IFNAR1 component that comprises amino acids 28-436 or 28-335 of SEQ ID NO:2, or a fragment thereof, optionally modified with one or more modifications defined in modification group I, and R2 is an IFNAR2 component comprising 27-243 or 35-233 of SEQ ID NO:4, or a fragment thereof, optionally modified with one or more of the modifications of modification group II. Optionally, $(R1)_x$-$(R2)_y$-F further comprises a signal sequence (SS).

R1: Naturally occurring wild-type IFNAR1 protein is a 557-amino acid protein having the amino acid sequence of the extracellular domain shown in SEQ ID NO:2 with signal sequence included at 1-27. In one embodiment, R1 comprises amino acids 28-436 of SEQ ID NO:2 optionally further modified by one or more modifications listed in modification group 1. In another embodiment, R1 comprises amino acids 28-335 of SEQ ID NO:2, or a fragment thereof, optionally comprising at least one of modification from modification group I.

Modification Group I: an amino acid at position S90, S91, L92, K93, V96, Y97, W156, L305, R306, and/or V307 of SEQ ID NO:2 is replaced with a different amino acid.

R2: Naturally occurring human wild-type IFNAR2 protein is a 515-amino acid protein having the amino acid sequence of the extracellular domain shown in SEQ ID NO:4 with signal sequence included at 1-26. In one embodiment, R2 comprises amino acids 27-243 of SEQ ID NO:4 optionally with at least one of the modification selected from those listed in modification group II. In another embodiment, R2 comprises 35-233 of SEQ ID NO:4, or a fragment thereof, optionally modified with one or more of the modifications listed in modification group II.

Modification Group II: amino acid at position M73, P76, L79, V107, V109, W127, I130, E111, S123, H124, N125, D131, D165, D216, E77, K75, E104, H103, Y70, W99, Y106, I72, L95, F126, and/or L128 of SEQ ID NO:4 is (are) replaced with a different amino acid.

The optional fusion component (F) comprises any component that enhances the functionality of the fusion protein. Thus, for example, a fusion component may enhance the biological activity of the fusion protein, aid in its production and/or recovery, or enhance a pharmacological property or the pharmacokinetic profile of the fusion protein by, for example, enhancing its serum half-life, tissue penetrability, lack of immunogenicity, or stability. In preferred embodiments, the fusion component is selected from the group consisting of a multimerizing component, a serum protein, or a molecule capable of binding a serum protein.

When the fusion component is a multimerizing component, the fusion component includes any natural or synthetic sequence capable of interacting with any other multimerizing component to form a higher order structure, e.g., a dimer, a trimer, etc. In specific embodiments, the multimerizing component is selected from the group consisting of (i) an immunoglobulin-derived domain, (ii) an amino acid sequence between 1 to about 500 amino acids in length, optionally comprising at least one cysteine residue, (iii) a leucine zipper, (iv) a helix loop motif, and (v) a coil-coil motif. In a specific embodiment, the immunoglobulin-derived domain is selected from the group consisting of the Fc domain of IgG or the heavy chain of IgG. In another specific embodiment, the Fc domain of IgG is human FcΔ1(a), an Fc molecule comprising a mutation of the region involved in forming the disulfide bond with the light chain.

When the fusion component is a serum protein, the serum protein may be any serum protein or a fragment of a serum protein. When the fusion component is a molecule capable of binding a serum protein, it may be a small molecule, a nucleic acid, a peptide, or an oligosaccharide. The fusion component may also be a protein such as Fc gamma R1, ScFv, etc. In preferred embodiments, the fusion component is encoded by the nucleic acid that encodes the fusion protein of the invention. In some embodiments, however, such as when the fusion component is an oligosaccharide, the fusion component is attached post-translationally to the expressed fusion protein.

The nucleic acid molecule of the invention may further optionally comprise a signal sequence (SS) component. When a SS is part of the polypeptide, any SS known to the art may be used, including synthetic or natural sequences from any source, for example, from a secreted or membrane bound protein. In a preferred embodiment, an ROR signal sequence is used (SEQ ID NO:5).

In specific embodiments, the invention features a nucleic acid molecule encoding an interferon α- and/or interferon β-binding fusion protein, including nucleic acid molecules encoding an amino acid sequence selected from the group consisting of SEQ ID NO:6 ($R2_{27-243}$-$R1_{28-436}$-Fc) and SEQ ID NO:9 ($R2_{35-233}$-$R1_{28-335}$-Fc). In one embodiment, the nucleic acid molecule of the invention encodes a fusion protein capable of binding interferon α2a (IFNα2a).

In a related second aspect, the invention features a vector comprising a nucleic acid molecule of the invention. In third and fourth aspects, the invention encompasses expression vectors comprising the nucleic acid molecules operatively linked to an expression control sequence, and host-vector systems for the production of a fusion protein that comprise the expression vector, in a suitable host cell; host-vector systems, wherein the suitable host cell is, without limitation, a bacterial, yeast, insect, mammalian or plant cell, such as tobacco; or animals such as cows, mice, or rabbits. Examples of suitable cells include E. coli, B. subtilis, BHK, COS and CHO cells. Fusion proteins modified by acetylation or pegylation are also encompassed by the invention.

In a fifth aspect, the invention features a method of producing a fusion protein of the invention, comprising culturing a host cell transfected with a vector wherein the vector comprises a nucleic acid molecule of the invention, under conditions suitable for expression of the protein from the host cell, and recovering the protein so produced.

In a sixth aspect, the invention features an interferon α- and/or β-binding fusion protein comprising $(R1)_x$-$(R2)_y$-F, wherein R1, R2, F, x and y are as described above. X and y are preferably each a number between 1-3; preferably x and y are each 1. In specific embodiments, the fusion protein is an amino acid sequence selected from the group consisting of SEQ ID NO:6 and 9.

In a seventh aspect, the invention features a multimeric polypeptide, comprising two or more fusion proteins of the invention. In a specific embodiment, the multimeric polypeptide is a dimer. The dimeric interferon α- and/or β-binding fusion proteins of the invention are capable of binding interferon α and/or β ("α/β") with an affinity of at least $10^{-8}$ M, as determined by assay methods known in the art. Generally, the ability of the dimeric interferon α/β-binding fusion proteins to inhibit (e.g., block) the biological activity of interferon α/β, may be measured, for example, by bioassay, such as an ELISA assay, for free and/or bound ligand. Bioassays may include luciferase-based assays using an ISRE promoter element, and/or interferon α/β stimulation of cell lines such as plasmocytoid dendritic cells (PDCs). Alternatively, a bioassay may involve the inhibition of the growth-inhibitory effect of interferon on cell lines such as Daudi.

In an eighth aspect, the invention features pharmaceutical compositions comprising a fusion protein of the invention with a pharmaceutically acceptable carrier. Such pharmaceutical compositions may comprise a monomeric or multimeric polypeptide, or nucleic acids encoding the fusion protein.

The interferon α/β-binding polypeptides of the invention are therapeutically useful for treating any disease or condition which is improved, ameliorated, or inhibited by removal, inhibition, or reduction of interferon α and or interferon β. These polypeptides are particularly useful for the treatment of autoimmune diseases, such as systemic lupus erythematosus (SLE) or insulin-dependent diabetes mellitus (IDDM), which are improved, ameliorated, or inhibited by removal, inhibition, or reduction of interferon α/β. Accordingly, in a further aspect, the invention features a therapeutic method for the treatment of an interferon α/β-related disease or condition, comprising administering a fusion protein of the invention to a subject suffering from an interferon α/β-related disease or condition. Although any mammal can be treated by the therapeutic methods of the invention, the subject is preferably a human patient suffering from or at risk of suffering from a condition or disease which can be improved, ameliorated, inhibited or treated with a fusion protein of the invention.

Other objects and advantages will become apparent from a review of the ensuing detailed description.

DETAILED DESCRIPTION OF THE INVENTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to describe the methods and/or materials in connection with which the publications are cited.

Definitions

The term "affinity for" interferon α/β means that the multimeric fusion proteins of the invention binds the intended cytokine(s) with an affinity of at least $10^{-8}$ M, preferably at least $10^{-9}$ M, even more preferably at least $10^{-10}$ M as determined by assay methods known in the art, for example, surface plasmon resonance, e.g., Biacore™ analysis. In some cases, binding to a specific cytokine (for example, α2) will be preferred.

The term "human interferon α" includes 23 or more closely related proteins encoded by distinct genes with a high degree of structural homology (Weismann et al (1986) Prog. Nucl. Acid. Res. Mol, Biol. 33:251 and (1993) J. Inteferon Res. 13; 443-444; Roberts et al (1998) J. Interferon Cytokine Res. 18:805-816). The multimers of the invention preferably bind and inhibit interferon α2a, and may bind and inhibit other members of the interferon α family of proteins. The term "capable of specifically blocking interferon α" or "capable of inhibiting the activity of interferon α" and/or "capable of specifically blocking interferon β" or "capable of inhibiting the activity of interferon β", means the interferon α/β-binding fusion proteins of the invention form multimers that inhibit the biological activity of the target cytokines, as measured, for example, by bioassay such as, for example, an ELISA assay, for free and/or bound ligand. Bioassays may include luciferase-based assays using an ISRE promoter element, and/or interferon α and or interferon β stimulation of cell lines such as PDCs. "IC50" is defined as the concentration of fusion protein required to inhibit 50% of the response to interferon α as measured in a bioassay. The multimeric fusion protein of the invention is capable of specifically binding to interferon α2a, with an affinity of at least about $10^{-9}$ M, or preferably at least about $3\times10^{-10}$ M, and/or is capable of specifically binding to interferon β with an affinity of at least about $10^{-10}$ M, or preferably at least about $5\times10^{-11}$ M as determined by Biacore™ analysis. Alternatively, the ability of the multimeric polypeptide of the invention to inhibit interferon α and β activities may be expressed as IC50 which is the concentration of interferon α/β-specific multimeric protein that inhibits 50% of interferon α/β activity, as measured, for example, in a bioassay such as the ISRE-luciferase assay described below. The interferon α/β-specific multimeric polypeptides of the invention exhibit an IC50 in an interferon α2a assay of $1\times10^{-8}$ M, more preferably $1\times10^{-9}$ M, and in an interferon β bioassay of $1\times10^{-9}$ M, more preferably $1\times10^{-10}$ M.

The terms "treatment", "treating", and the like are used herein to generally include obtaining a desired pharmacologic and/or physiologic effect. The effect may be prophylactic in terms of completely or partially preventing a disease, condition, or symptoms thereof, and/or may be therapeutic in terms of a partial or complete cure for a disease or condition and/or adverse effect attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; or (c) relieving the disease or condition, i.e., causing regression of the disease or condition. The population of subjects treated by the method of the invention includes subjects suffering from the undesirable condition or disease, as well as subjects at risk for development of the condition or disease.

By the term "therapeutically effective dose" is meant a dose that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding).

As used herein, a "condition or disease" generally encompasses a condition of a mammalian host, particularly a human host, which is undesirable and/or injurious to the host. Thus, treating a condition or disorder with an interferon α- and/or interferon β-binding fusion protein will encompass the treatment of a mammal, in particular, a human, who has symptoms reflective of elevated or deleterious interferon α/β, or who is expected to have such decreased activation in response to a disease, condition or treatment regimen. Treating an interferon α/β-related condition or disease encompasses the treatment of a human subject wherein reducing interferon α/β levels with the fusion protein of the invention results in amelioration of an undesirable symptom resulting from the interferon α/β-related condition or disease.

General Description

Studies in animals lacking interferon α/β have indicated that these cytokines play both overlapping and additive roles in the resistance to viral infections, inhibit cell proliferation and regulate expression of MHC class I. Elevated interferon α correlates with the development of human autoimmune disease (for review, see Stewart et al. (2003) Cytokine & Growth Factor Reviews 14:139-154). There is a very good correlation between the presence of interferon α and SLE and IDDM. Interferon a has also been associated with psoriasis (Schmid et al. (1994) J. Interferon Res. 14:229-234) and Crohn's disease (Fais et al. (1994) J. Interferon Res. 14:235-238). The present invention provides novel polypeptides, both monomers and multimers, capable of acting as interferon α/β-binding fusion proteins or antagonists capable of binding interferon α/β and blocking these biological actions.

Nucleic Acid Constructs and Expression

The present invention provides for the construction of nucleic acid molecules encoding interferon α/β-binding polypeptides. As described above, the nucleic acid molecules of the invention encode modified fragments of the wild-type (or naturally occurring) human IFNAR1 and/or IFNAR2 proteins. Accordingly, the nucleic acid molecules may be termed "recombinant", "artificial", or "synthetic" as they are not nucleic acid molecules found in nature, e.g., not naturally occurring sequences, but are sequences constructed by recombinant DNA technology.

These nucleic acid molecules are inserted into a vector that is able to express the fusion proteins of the invention when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the fusion proteins of the invention under control of transcriptional and/or translational control signals.

Expression of the nucleic acid molecules of the invention may be regulated by a second nucleic acid sequence so that the molecule is expressed in a host transformed with the recombinant DNA molecule. For example, expression may be controlled by any promoter/enhancer element known in the art. Promoters which may be used to control expression of the chimeric polypeptide molecules include, but are not limited to, a long terminal repeat (Squinto et al. (1991) Cell 65:1-20); SV40 early promoter region, CMV, M-MuLV, thymidine kinase promoter, the regulatory sequences of the metallothionine gene; prokaryotic expression vectors such as the beta-lactamase promoter, or the tac promoter (see also Scientific American (1980) 242:74-94); promoter elements from yeast or other fungi such as Gal 4 promoter, ADH, PGK, alkaline phosphatase, and tissue-specific transcriptional control regions derived from genes such as elastase I.

Expression vectors capable of being replicated in a bacterial or eukaryotic host comprising the nucleic acid molecules of the invention are used to transfect the host and thereby direct expression of such nucleic acids to produce the fusion proteins of the invention. Transfected cells may transiently or, preferably, constitutively and permanently express the polypeptides of the invention. When the polypeptide so expressed comprises a fusion component such as a multimerizing component capable of associating with a multimerizing component of a second polypeptide, the monomers thus expressed multimerize due to the interactions between the multimerizing components to form a multimeric polypeptide (WO 00/18932, herein specifically incorporated by reference).

The fusion proteins of the invention may be purified by any technique known in the art. When the polypeptides of the invention comprise a multimerizing component, which spontaneously forms a multimer with another polypeptide, the purification techniques used allow for the subsequent formation of a stable, biologically active multimeric polypeptide, also known as a "fusion protein". For example, and not by way of limitation, the factors may be recovered from cells either as soluble proteins or as inclusion bodies, from which they may be extracted quantitatively by 8M guanidinium hydrochloride and dialysis (see, for example, U.S. Pat. No. 5,663,304). In order to further purify the factors, conventional ion exchange chromatography, hydrophobic interaction chromatography, reverse phase chromatography or gel filtration may be used.

R1 and R2 Components

Interferon α and interferon β bind to a common receptor sometimes known as the IFNα/βR made up of two subunits (IFNAR1 and IFNAR2). Naturally occurring wild-type IFNAR1 protein is a 557-amino acid protein having the extracellular amino acid sequence of SEQ ID NO:2 (shown with signal sequence). R1 is an IFNAR1-derived component having amino acids 28-436 or amino acids 28-335 of SEQ ID NO:2, or a fragment thereof. Naturally occurring human wild-type IFNAR2 protein is a 515-amino acid protein having the amino acid sequence of the extracellular domain shown in SEQ ID NO:4. R2 is an IFNAR2-derived component having amino acids 27-243 or amino acids 35-233 of SEQ ID NO:4, or a fragment thereof. Optionally, either or both components can be further modified to provide fusion proteins with specifically desired properties, such as, for example, improved solubility, reduced immunogenicity, improved PK, improved production characteristics, and/or improved ability to block interferon α and/or interferon β activity.

Fusion Components

The fusion proteins of the invention comprise a fusion component (F) that, in specific embodiments, is selected from the group consisting of a multimerizing component, a serum protein, or a molecule capable of binding a serum protein. When F comprises a multimerizing component, it includes any natural or synthetic sequence capable of interacting with another multimerizing component to form a higher order structure, e.g., a dimer, a trimer, etc. The multimerizing component may be selected from the group consisting of (i) a multimerizing component, (ii) a truncated multimerizing component, (iii) an amino acid sequence between 1 to about 500 amino acids in length, (iv) a leucine zipper, (v) a helix loop motif, and (vi) a coil-coil motif. When F is a multimerizing component comprising an amino acid sequence between 1 to about 500 amino acids in length, the sequence may contain one or more cysteine residues capable of forming a disulfide bond with a corresponding cysteine residue on another fusion protein comprising an F with one or more cysteine residues.

In a preferred embodiment, the multimerizing component comprises one or more immunoglobulin-derived domains from human IgG, IgM or IgA. In specific embodiments, the immunoglobulin-derived domain is selected from the group consisting of the Fc domain of IgG or the heavy chain of IgG. The Fc domain of IgG may be selected from the isotypes IgG1, IgG2, IgG3, and IgG4, as well as any allotype within each isotype group. In a specific embodiment, F is the Fc domain of IgG4 with Ser228 (Kabat numbering) mutated to Pro to stabilize covalent dimer formation (Mol. Immunol. (1993) 30:105-108) and/or Leu235→Glu which eliminates residual effector functions (Reddy et al. (2000) J. Immunol. 164:1925-1933). In a preferred embodiment, F is the Fc domain of IgG1, or a derivative thereof which may be modified for specifically desired properties (see, for example, Armour et al. (2003) Mol. Immunol. 40:585-593; Shields et al. (2001) J. Biol. Chem. 276:6591-6604). In specific embodiments, the interferon α/β-binding polypeptide of the invention comprises one or two Fc domain(s) of IgG1.

In one embodiment, F is a serum protein or fragment thereof and is selected from the group consisting of α-1-microglobulin, AGP-1, orosomuciod, α-1-acid glycoprotein, vitamin D binding protein (DBP), hemopexin, human serum albumin (hSA), transferrin, ferritin, afamin, haptoglobin, α-fetoprotein thyroglobulin, α-2-HS-glycoprotein, β-2-glycoprotein, hyaluronan-binding protein, syntaxin, C1R, C1q a chain, galectin3-Mac2 binding protein, fibrinogen, polymeric Ig receptor (PIGR), α-2-macroglobulin, urea transport protein, haptoglobin, IGFBPs, macrophage scavenger receptors, fibronectin, giantin, Fc, α-1-antichyromotrypsin, α-1-antitrypsin, antithrombin III, apolipoprotein A-I, apolipoprotein B, β-2-microglobulin, ceruloplasmin, complement component C3 or C4, CI esterase inhibitor, C-reactive protein, cystatin C, and protein C. In a specific embodiment, F is selected from the group consisting of α-1-microglobulin, AGP-1, orosomuciod, α-1-acid glycoprotein, vitamin D binding protein (DBP), hemopexin, human serum albumin (hSA), afamin, and haptoglobin. The inclusion of an F component may extend the serum half-life of the interferon α/β-binding polypeptide of the invention when desired. See, for example, U.S. Pat. Nos. 6,423,512, 5,876,969, 6,593,295, and 6,548,653, herein specifically incorporated by reference in their entirety, for examples of serum albumin fusion proteins. hSA is widely distributed throughout the body, particularly in the intestinal and blood components, and has an important role in the maintenance of osmolarity and plasma volume. It is slowly cleared in the liver, and typically has an in vivo half-life of 14-20 days in humans (Waldmann et al. (1977) *Albumin, Structure Function and Uses*; Pergamon Press; pp. 255-275).

When F is a molecule capable of binding a serum protein, the molecule may be a synthetic small molecule, a lipid or liposome, a nucleic acid, including a synthetic nucleic acid such as an aptomer, a peptide, or an oligosaccharide. The molecule may further be a protein, such as, for example, FcγR1, FcγR2, FcγR3, polymeric Ig receptor (PIGR), ScFv, and other antibody fragments specific for a serum protein.

Optional Spacers

Components of the fusion proteins of the invention may be connected directly to each other or be connected via spacers. Generally, the term "spacer" (or linker) means one or more molecules, e.g., nucleic acids or amino acids, or non-peptide moieties, such as polyethylene glycol, which may be inserted between one or more component domains. For example, spacer sequences may be used to provide a desirable site of interest between components for ease of manipulation. A spacer may also be provided to enhance expression of the fusion protein from a host cell, to decrease steric hindrance such that the component may assume its optimal tertiary structure and/or interact appropriately with its target molecule. For spacers and methods of identifying desirable spacers, see, for example, George et al. (2003) Protein Engineering 15:871-879, herein specifically incorporated by reference. A spacer sequence may include one or more amino acids naturally connected to a receptor component, or may be an added sequence used to enhance expression of the fusion protein, provide specifically desired sites of interest, allow component domains to form optimal tertiary structures and/or to enhance the interaction of a component with its target molecule. In one embodiment, the spacer comprises one or more peptide sequences between one or more components that are between 1-100 amino acids, preferably 1-25. In a specific embodiment, the spacer is a two amino acid sequence. The two amino acid sequence can be Ser Gly or Arg Ser.

Inhibition of Interferon α/β Biological Activity

The fusion proteins of the invention are capable of inhibiting the biological activity of interferon α with an IC50 (concentration of fusion protein required to inhibit 50% of the response to interferon α/β) of at least $1\times10^{-8}$ M, more preferably $1\times10^{-9}$ M for interferon α2a, and in an interferon β bioassay of $1\times10^{-9}$ M, more preferably $1\times10^{-10}$ M in an ISRE luciferase assay. Other bioassays useful to determine IC50 are known to the art, including, for example, Daudi viability, and/or interferon α/β stimulation of PDCs.

Therapeutic Uses

The fusion proteins of the invention are therapeutically useful for treating any disease or condition which is improved, ameliorated, inhibited or prevented by removal, inhibition, or reduction of one or both of interferon α and β. Interferon α and interferon β both independently, and jointly, have been implicated in a variety of clinical conditions, such as SLE and IDDM. Accordingly, the blocking of these responses by the fusion protein will be useful for the treatment of any disease or condition in which there is increased level of interferon α/β.

In one embodiment, the interferon α/β-binding fusion protein is used to treat SLE. Data derived from animal experiments and examination of humans suffering from SLE implicate interferon α. Patients with SLE have ongoing interferon α production and serum interferon α levels are correlated with both diseases activity and severity (Ronnblom and Alm (2003) Arthritis Res. Ther. 5:68-75).

Suitable Subject for Treatment

A suitable subject for treatment is a human diagnosed as suffering from specific conditions improved by inhibition or reduction of interferon α/β, including autoimmune diseases such as SLE or IDDM.

Combination Therapies

In numerous embodiments, the fusion proteins of the invention may be administered in combination with one or more additional compounds or therapies. For example, multiple fusion proteins can be co-administered, or one polypeptide can be administered in conjunction with one or more therapeutic compounds. When a polypeptide of the invention binds interferon α/β, the one or more other therapeutic agent is one that is used to prevent or treat a condition associated with the presence of interferon α/β. A benefit of the combined use of the fusion protein of the invention with a second therapeutic agent is that combined use can provide improved efficacy and/or reduced toxicity of either therapeutic agent.

Methods of Administration

The invention provides methods of treatment comprising administering to a subject an effective amount of a fusion protein of the invention. In a preferred aspect, the fusion protein is substantially purified (e.g., substantially free from substances that limit its effect or produce undesired side-effects). The subject is preferably a mammal, and most preferably a human.

Various delivery systems are known and can be used to administer an agent of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intra-articular, infusion proteineritoneal, intravenous, subcutaneous, intranasal, intraocular, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Administration can be acute or chronic (e.g. daily, weekly, monthly, etc.) or in combination with other agents. Pulmonary administration can also be employed, e.g., by use of an inhaler or nebulizer, and formulation with an aerosolizing agent.

In another embodiment, the active agent can be delivered in a vesicle, in particular a liposome, in a controlled release system, or in a pump. In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), by direct injection, or by use of microparticle bombardment, or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination. Systemic expression may also be achieved by plasmid injection (intradermally or intramuscularly) and electroporation into cells.

In a specific embodiment, the pharmaceutical compositions of the invention are administered locally to an area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes.

A composition useful in practicing the methods of the invention may be a liquid comprising an agent of the invention in solution, in suspension, or both. The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment.

In one embodiment, the pharmaceutical composition of the invention is a sustained release composition. Sustained release formulations for delivery of biologically active peptides are known to the art. For example, U.S. Pat. No. 6,740,634, herein specifically incorporated by reference in its entirety, describes a sustained-release formulation containing a hydroxynaphtoic acid salt of a biologically active substance and a biodegradable polymer. U.S. Pat. No. 6,699,500, herein specifically incorporated by reference in its entirety, discloses a sustained-release formulation capable of releasing a physiologically active substance over a period of at least 5 months.

Diagnostic and Screening Methods

The fusion proteins of the invention may be used diagnostically and/or in screening methods. For example, the fusion protein may be used to monitor levels of interferon α/β during a clinical study to evaluate treatment efficacy. In another embodiment, the methods and compositions of the present invention are used to screen individuals for entry into a clinical study to identify individuals having, for example, too high or too low a level of interferon α/β. The fusion proteins of the invention can be used in methods known in the art relating to the localization and activity of interferon α/β, e.g., imaging, measuring levels thereof in appropriate physiological samples, in diagnostic methods, etc.

The fusion proteins of the invention may be used in in vivo and in vitro screening assays to quantify the amount of non-bound interferon α/β present, e.g., for example, in a screening method to identify test agents able to decrease the expression of interferon α/β. More generally, the fusion proteins of the invention may be used in any assay or process in which quantification and/or isolation of interferon α/β is desired.

Pharmaceutical Compositions

The present invention also provides pharmaceutical compositions comprising a fusion protein of the invention. Such compositions comprise a therapeutically effective amount of one or more fusion protein(s), and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin.

The fusion protein of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the fusion protein that will be effective for its intended therapeutic use can be determined by standard clinical techniques based on the present description. In addition, in vitro assays may optionally be employed to help identify optimal dosage ranges. Generally, suitable dosage ranges for intravenous administration are generally about 0.02-10 milligrams active compound per kilogram body weight. Suitable dosage ranges for intranasal administration are generally about 0.01 pg/kg body weight to 10 mg/kg body weight. Effective doses may be extrapolated from dose-response curves derived from in vitro or animal model test systems. The amount of compound administered will, of course, be dependent on the subject being treated, on the subject's weight, the severity of the affliction, the manner of administration, and the judgment of the prescribing physician. The therapy may be repeated intermittently while symptoms are detectable or even when they are not detectable.

Cellular Transfection and Gene Therapy

The present invention encompasses the use of nucleic acids encoding the fusion proteins of the invention for transfection of cells in vitro and in vivo. These nucleic acids can be inserted into any of a number of well-known vectors for transfection of target cells and organisms. The nucleic acids are transfected into cells ex vivo and in vivo, through the interaction of the vector and the target cell facilitated by lipid mixes or electroporation. The compositions are administered (e.g., by injection into a muscle) to a subject in an amount sufficient to elicit a therapeutic response. An amount adequate to accomplish this is defined as "a therapeutically effective dose or amount."

In another aspect, the invention provides a method of reducing interferon α/β levels in a human or other animal comprising transfecting a cell with a nucleic acid encoding a polypeptide of the invention, wherein the nucleic acid comprises an inducible promoter operably linked to the nucleic acid encoding the polypeptide. For gene therapy procedures in the treatment or prevention of human disease, see for example, Van Brunt (1998) Biotechnology 6:1149-1154.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Construction of Interferon α/β-Binding Fusion Proteins

To create the parental interferon α/β-binding fusion protein, R2-R1-Fc (SEQ ID NO:6 and SEQ ID NO:9) nucleic acid encoding the human IFNAR1 extracellular domain (SEQ ID NO:2) and the human IFNAR2 extracellular domain (SEQ ID NO:4), each component having a N-terminal two amino acid restriction linker, were amplified using standard PCR techniques, and were ligated into an expression vector which contained the human Fc sequence, thus creating a fusion protein having the IFNAR1 and/or IFNAR2, and the hinge, CH2 and CH3 regions of human IgG1 from the N to C terminus. All sequences were verified by standard molecular biology techniques. The appropriate coding sequence was subcloned into a eukaryotic expression vector using standard molecular biology techniques.

Interferon α/β-binding fusion protein variants are created by site-directed mutagenesis of the parent fusion protein using techniques known to the art, and confirmed by sequencing.

Example 2

Determination of Interferon α/β Binding Affinity

The affinity of the interferon α/β-binding fusion proteins for human interferon α2A and human interferon β is measured using surface plasmon resonance (Biacore 2000™ or Biacore 3000™, as described in WO00/75319, herein specifically incorporated by reference in its entirety. Briefly, the interferon α/β-binding fusion proteins of the invention are captured onto the chip surface using anti-human Fc antibodies. Various concentrations of human interferon α and/or β are injected over the surface and the time course of association and dissociation are monitored. Kinetic analyses using BIA evaluation software are performed to obtain the association and dissociation rate constants.

The Biacore assays for the parental R2-R1-Fc (SEQ ID NO:6) construct relative to R1-Fc (SEQ ID NO:7) and R2-Fc (SEQ ID NO:8) were conducted. R1-Fc was found to have minimal binding activity. Table 1 shows the results obtained with R2-Fc, R2-R1-Fc, and R2(35-233)-R1(28-335)-Fc.

TABLE 1

| Construct | Ligand | $K_D$ |
|---|---|---|
| R2-Fc (SEQ ID NO: 8) | IFNα-2a | $1.0 \times 10^{-8}$ M |
|  | IFNβ | $8.3 \times 10^{-9}$ M |
| R2-R1-Fc (SEQ ID NO: 6) | IFNα-2a | $1.2 \times 10^{-10}$ M |
|  | IFNβ | $3.99 \times 10^{-11}$ M |
| R2(35-233)-R1(28-335)-Fc (SEQ ID NO: 9) | IFNα-2a | $2.85 \times 10^{-10}$ M |
|  | IFNβ | $8.29 \times 10^{-12}$ M |

Example 3

Inhibition of Interferon α/β Bioactivity by Interferon α/β-Binding Fusion Proteins HEK 293 cells transiently transfected with an ISRE-luciferase expression vector were used to determined the inhibitory effect of the fusion proteins of the invention on interferon α and interferon β activity. Briefly, HEK293 cells were transiently transfected using lipofectamine with a vector containing an ISRE-luciferase expression cassette. After 3 days at 37° C. various concentrations of interferon α/β-binding fusion proteins were added along with 50 pM of IFN-2A or IFN-β. The cells were then incubated at 37° C., with 5% $CO_2$ for 6 hours and the luciferase activity was determined using Steady-Glo, following the manufacturers instructions (Promega). IC50 values were determined as the concentration of interferon α/β-binding fusion protein that blocked 50% of the activity of interferon α or interferon β, and the values are shown in Table 2.

TABLE 2

| Construct | Ligand | IC50 |
|---|---|---|
| R2-Fc (SEQ ID NO: 8) | IFNα-2a | $4.93 \times 10^{-8}$ M |
|  | IFNβ | $5.48 \times 10^{-8}$ M |
| R2-R1-Fc (SEQ ID NO: 6) | IFNα-2a | $2.93 \times 10^{-9}$ M |
|  | IFNβ | $8.31 \times 10^{-11}$ M |
| R2(35-233)-R1(28-335)-Fc (SEQ ID NO: 9) | IFNα-2a | $4.91 \times 10^{-9}$ M |
|  | IFNβ | $1.12 \times 10^{-10}$ M |

Alternatively, the inhibition of interferon α/β bioactivity by interferon α and interferon β-binding fusion proteins of the invention can be measured in Daudi cells. Briefly, Daudi cells are grown the presence of variable concentrations of interferon α/β-binding fusion proteins and 9 pM of human interferon 2a. Three days following IFN-2a addition, cell number is quantitated using CCK-8, following the manufacturers instructions (Dojindo). No inhibition was observed with R2-Fc, whereas R2-R1-Fc exhibited an IC50 of about $1.3-3.3 \times 10^{-8}$ M.

We claim:

1. A fusion protein comprising consisting of R2, R1 and F, in the N-terminus to C-terminus direction, and optionally a spacer sequence at one or more positions selected from the group consisting of: (i) between R2 and R1 and (ii) between R1 and F, wherein:

R2 consists of amino acids 35-233 of SEQ ID NO:4;

R1 consists of amino acids 28-335 of SEQ ID NO:2;

F consists of an immunoglobulin-derived domain selected from the group consisting of an Fc domain of IgG and a heavy chain of IgG; and each spacer sequence consists of Ser-Gly or Arg-Ser.

2. A nucleic acid molecule encoding the fusion protein of claim 1.

3. A vector comprising the nucleic acid molecule of claim 2.

4. A host cell comprising the vector of claim 3.

5. A method of producing a fusion protein, comprising culturing the host cell of claim 4 under conditions suitable for expression of the fusion protein from the host cell, and recovering the fusion protein so produced.

6. the fusion protein of claim 1, wherein each spacer sequence is Ser-Gly or Arg-Ser.

7. A fusion protein comprising an amino acid sequence selected from the group consisting of SEQ ID NO:6 and SEQ ID NO:9.

8. A multimeric protein comprising two of the fusion proteins of claim 7.

9. A nucleic acid molecule encoding the fusion protein of claim 7.

10. A host cell comprising the nucleic acid molecule of claim 9.

11. A method of producing a fusion protein, comprising culturing the host cell of claim 10 under conditions suitable for expression of the fusion protein from the host cell, and recovering the fusion protein so produced.

12. A fission protein comprising consisting of R2, R1 and F, in the N-terminus to C-terminus direction, and optionally a spacer sequence at one or more positions selected from the group consisting of: (i) between R2 and R1 and (ii) between R1 and F, wherein:

R2 comprises amino acids 27-243 of SEQ ID NO:4;

R1 comprises amino acids 28-335 of SEQ ID NO:2; and,

F comprises an immunoglobulin-derived domain selected from the group consisting of an Fc domain of IgG and a heavy chain of IgG.

13. The fusion protein of claim 12, wherein R1 comprises amino acids 28-436 of SEQ ID NO:2.

14. The fusion protein of claim 12, further comprising a signal sequence at the N-terminus of the fusion protein.

15. A multimeric protein comprising two of the fusion proteins of claim 12.

16. A nucleic acid molecule encoding the fusion protein of claim 12.

17. A vector comprising the nucleic acid molecule of claim 16.

18. A host cell comprising the vector of claim 17.

19. A method of producing a fusion protein, comprising culturing the host cell of claim 18 under conditions suitable for expression of the fusion protein from the host cell, and recovering the fusion protein so produced.

20. The fusion protein of claim 12, wherein each spacer sequence comprises Ser-Gly or Arg-Ser.

* * * * *